(12) United States Patent
Wagner et al.

(10) Patent No.: US 7,317,065 B2
(45) Date of Patent: Jan. 8, 2008

(54) METHOD FOR PRODUCING HIGHLY FUNCTIONAL, HYPER BRANCHED POLYESTER BY MEANS OF ENZYMATIC ESTERIFICATION

(75) Inventors: Eva Wagner, Speyer (DE); Bernd Bruchmann, Freinsheim (DE); Dietmar Haering, Schriesheim (DE); Peter Keller, Spiesen-Elversberg (DE); Thomas Pouhe, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 11/405,426

(22) Filed: Apr. 18, 2006

(65) Prior Publication Data

US 2006/0211842 A1    Sep. 21, 2006

Related U.S. Application Data

(62) Division of application No. 10/497,535, filed as application No. PCT/EP02/14454 on Dec. 18, 2002, now Pat. No. 7,081,509.

(30) Foreign Application Priority Data

Dec. 20, 2001 (DE) .................. 101 63 163

(51) Int. Cl.
*C08G 63/00* (2006.01)
(52) U.S. Cl. ............... 528/176; 156/230; 156/241; 156/247; 428/343; 428/354; 524/556; 524/558; 524/588; 524/589
(58) Field of Classification Search ............ 156/230, 156/241, 247; 428/343, 354; 524/556, 558, 524/588, 589; 528/176
See application file for complete search history.

(56) References Cited

U.S. PATENT DOCUMENTS 6,562,603 B2 * 5/2003 Bramucci et al. ........... 435/146

OTHER PUBLICATIONS

T. Tsujimoto, et al., "Enzymatic Synthesis of Cross-Linkable Polyesters From Renewable Resources", American Chemical Society, 2001.
S. Wada, et al., "The Synthesis of Hyperbranched Polyesters by Enzyme-Catalyzed Polymeration", pp. 1-5.

* cited by examiner

*Primary Examiner*—Terressa Boykin
(74) *Attorney, Agent, or Firm*—Oblon, Spivak, McClelland, Maier & Neustadt, P.C.

(57) ABSTRACT

The present invention provides a highly functional hyperbranched polyester which may be obtained by a process which comprises reacting a reaction solution containing solvent and reactants in the presence of an enzyme at a temperature above 60° C. and a pressure above 500 mbar.

23 Claims, No Drawings

METHOD FOR PRODUCING HIGHLY FUNCTIONAL, HYPER BRANCHED POLYESTER BY MEANS OF ENZYMATIC ESTERIFICATION

CONTINIUNG APPLICATION INFORMATION

This application is a division of Ser. No. 10/497,535 filed Oct. 12, 2004 now U.S. Pat. No. 7,081,509 which is a 371 of PCT/EP02/14454 filed Dec. 18, 2002.

The present invention relates to a process for preparing highly functional hyperbranched polyesters which comprises reacting a reaction solution comprising solvent and (a) one or more dicarboxylic acids or one or more derivatives thereof with one or more at least trifunctional alcohols
(b) or one or more tricarboxylic acids or higher polycarboxylic acids or one or more derivatives thereof with one or more diols
(c) or one or more tricarboxylic acids or higher polycarboxylic acids or one or more derivatives thereof with one or more at least trifunctional alcohols
(d) or one or more di- or polyhydroxycarboxylic acids
(e) or one or more hydroxydi- or hydroxypolycarboxylic acids or mixtures of at least two of the above reaction solutions in the presence of an enzyme at temperatures above 60° C. and pressures above 500 mbar.

The present invention further relates to highly functional hyperbranched polyesters obtainable by the process described above and to the use of the resulting highly functional hyperbranched polyesters in coatings, paints, coverings, and adhesives.

Modified highly functional hyperbranched polyesters and polyester-based dendrimers are known per se from WO 96/19537, for example, and are already used in some applications, as impact modifiers, for example. But dendrimers are too expensive for general use, since the syntheses are exacting in their need for high yields in the constructional reactions and high purity in the intermediates and end products, and employ reagents which are too expensive for large-scale industrial use. The preparation of hyperbranched highly functional polyesters prepared by conventional esterification reactions normally requires very drastic conditions (cf. WO 96/19537) such as high temperatures and/or strong acids, for example. As a result, there may be side reactions such as dehydration reactions and decarboxylations, for example, and as a consequence of the side reactions there may be instances of unwanted resinification and discoloration.

Known esterification processes which are able to take place under gentle conditions include on the one hand those using very expensive activating reagents, such as dicyclohexylcarbodiimide, and using protective group chemistry, which is uneconomic in large-scale industrial reactions, and on the other hand enzymatic reactions, which do not provide the desired products, however. For instance, GB 2 272 904 discloses a process for the lipase-catalyzed preparation of a polyester by reacting at least one aliphatic dicarboxylic acid with at least one aliphatic diol or polyol or reacting at least one aliphatic hydroxycarboxylic acid with itself to form polyesters. The process is conducted at temperatures from 10 to 60° C., preferably from 40 to 45° C., and even when using glycerol gives preferentially unbranched polyesters (page 3 lines 26/27). The process disclosed in GB 2 272 904 can therefore be used for the targeted synthesis of linear polymers. Pentaerythritol cannot be reacted in processes disclosed in GB 2 272 904 (page 3 line 28). The example demonstrates the synthesis of a linear polyester from adipic acid and butane-1,4-diol.

WO 94/12652 discloses a process for enzyme-catalyzed synthesis of polyesters which is conducted in the absence of solvents (page 3 line 26). Two steps can be distinguished. In the first, oligomers are prepared enzymatically from diols and dicarboxylic acids or related products. Thereafter, either the enzyme is recovered and the reaction is continued at elevated temperature or the enzyme is left in the reaction mixture and the temperature is raised, with the risk of possible irreversible destruction of the enzyme.

In WO 98/55642 a special process for enzyme-catalyzed synthesis of polyesters by reacting either hydroxycarboxylic acids or else aliphatic dicarboxylic acids with aliphatic diols or polyols and, optionally, an aliphatic hydroxycarboxylic acid in a two-stage process, in the first stage of which—optionally in the presence of water—the starting products are reacted in the molar ratio of from 1:1 to 1.1:1 and, before the second stage, the supported enzyme is removed and recycled, the second stage being conducted at elevated temperature. The process disclosed does not effect reaction of sterically hindered secondary hydroxyl groups (page 7 lines 27/28), with the secondary hydroxyl group of glycerol, for example, being classed as sterically hindered (page 8 line 4), so that reaction of glycerol gives linear products.

WO 99/46397 discloses the synthesis of polyesters by reacting, for example, a polyol having two primary and at least one secondary alcohol function(s) with one or more dicarboxylic or tricarboxylic acids in the presence of an effective amount of a lipase, carried out preferably under reduced pressure, so that linear polyesters are obtained.

L. E. Iglesias et al. report in *Biotechnology Techniques* 1999, 13, 923 that linear polyesters are obtained by esterifying glycerol with adipic acid in the presence of an enzyme at 30° C.

B. I. Kline et al. report in *Polymer Mat. Sci. Eng.* 1998, 79, 35 that linear polyesters are obtained by reacting glycerol with divinyl adipate in the presence of an enzyme at 50° C.

On a poster at "The Second International Dendrimer Symposium", ids-2, Oct. 14-17, 2001, Tokyo University, Japan, H. Uyama reported the formation, during the reaction of polyazelaic anhydride with glycerol in the presence of *Candida antarctica* at 60° C. without solvent, first of linear oligomers. After 3 days a sharp increase in molecular weight was suddenly observed, and after 7 days the authors obtained a hyperbranched polyester having a molecular weight of 34,000 g/mol. Such drastic changes in the course of the reaction are, however, undesirable in large-scale industrial reactions, since they can lead to the reactions going out of control.

It is an object of the present invention to provide a process for preparing highly functional hyperbranched polyesters which avoids the disadvantages known from the prior art and prevents changes, especially uncontrolled changes, in reaction conditions. A further object is to provide novel highly functional hyperbranched polyesters. A last object is to provide novel uses for highly functional hyperbranched polyesters.

We have found that this object is achieved by the process defined at the outset.

The process of the invention comprises reacting reacting a reaction solution comprising (a) one or more dicarboxylic acids or one or more derivatives thereof with one or more at least trifunctional alcohols (b) or one or more tricarboxylic acids or higher polycarboxylic acids or one or more derivatives thereof with one or more diols (c) or one or more tricarboxylic acids or higher polycarboxylic acids or one or more derivatives thereof with one or more at least trifunctional alcohols (d) or one or more di- or polyhydroxycarboxylic acids (e) or one or more hydroxydi- or hydroxypolycarboxylic acids or mixtures of at least two of the above reaction solutions.

High-functionality hyperbranched polyesters for the purposes of the present invention are molecularly and structurally nonuniform. They differ in their molecular nonuniformity from dendrimers and are therefore much less complicated to prepare.

Dicarboxylic acids which can be reacted in reaction solutions according to variant (a) include for example oxalic acid, malonic acid, succinic acid, glutaric acid, adipic acid, pimelic acid, suberic acid, azelaic acid, sebacic acid, undecane-α,ω-dicarboxylic acid, dodecane-α,ω-dicarboxylic acid, cis- and trans-cyclohexane-1,2-dicarboxylic acid, cis- and trans-cyclohexane-1,3-dicarboxylic acid, cis- and trans-cyclohexane-1,4-dicarboxylic acid, cis- and trans-cyclopentane-1,2-dicarboxylic acid, and cis- and trans-cyclopentane-1,3-dicarboxylic acid, which dicarboxylic acids may be substituted by one or more radicals selected from $C_1$-$C_{10}$-alkyl groups, examples being methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-nonyl, and n-decyl, $C_3$-$C_{12}$-cycloalkyl groups, examples being cyclopropyl, cyclobutyl, cyclopentyl, cyclohexyl, cycloheptyl, cyclooctyl, cyclononyl, cyclodecyl, cycloundecyl, and cyclododecyl; cyclopentyl, cyclohexyl, and cycloheptyl are preferred;

alkylene groups such as methylene or ethylidene, or $C_6$-$C_{14}$-aryl groups such as phenyl, 1-naphthyl, 2-naphthyl, 1-anthryl, 2-anthryl, 9-anthryl, 1-phenanthryl, 2-phenanthryl, 3-phenanthryl, 4-phenanthryl, and 9-phenanthryl, for example, preferably phenyl, 1-naphthyl, and 2-naphthyl, with particular preference phenyl.

Exemplary representatives of substituted dicarboxylic acids include 2-methylmalonic acid, 2-ethylmalonic acid, 2-phenylmalonic acid, 2-methylsuccinic acid, 2-ethylsuccinic acid, 2-phenylsuccinic acid, itaconic acid, and 3,3-dimethylglutaric acid.

The dicarboxylic acids which can be reacted according to variant (a) further include ethylenically unsaturated acids such as maleic acid and fumaric acid, for example, and aromatic dicarboxylic acids such as phthalic acid, isophthalic acid or terephthalic acid, for example.

Additionally, mixtures of two or more of the abovementioned representatives may be used.

The dicarboxylic acids may be used either per se or in the form of derivatives.

By derivatives are meant preferably the corresponding anhydrides in monomeric or polymeric form, mixed anhydrides with other carboxylic acids, such as with acetic acid, monoalkyl or dialkyl esters, preferably monomethyl or dimethyl esters or the corresponding monoethyl or diethyl esters, but also the monoalkyl and dialkyl esters derived from higher alcohols such as n-propanol, isopropanol, n-butanol, isobutanol, tert-butanol, n-pentanol, and n-hexanol, for example, monovinyl and divinyl esters, and mixed esters, preferably methyl ethyl esters.

In the context of the present invention it is also possible to use a mixture of a dicarboxylic acid and one or more of its derivatives. It is also possible in the context of the present invention to use a mixture of two or more different derivatives of one or more dicarboxylic acids.

Particular preference is given to using succinic acid, glutaric acid, adipic acid, phthalic acid, isophthalic acid, terephthalic acid or their monomethyl or dimethyl esters. Very particular preference is given to using adipic acid. Very particular preference is likewise given to using commercially available mixtures of succinic, glutaric, and adipic acid.

At least trifunctional alcohols include for example glycerol, butane-1,2,4-triol, n-pentane-1,2,5-triol, n-pentane-1,3,5-triol, n-hexane-1,2,6-triol, n-hexane-1,2,5-triol, n-hexane-1,3,6-triol, trimethylolbutane, trimethylolpropane or ditrimethylolpropane, trimethylolethane, pentaerythritol or dipentaerythritol; sugar alcohols such as mesoerythritol, threitol, sorbitol or mannitol, for example, or mixtures of the at least trifunctional alcohols given above. It is preferred to use glycerol, trimethylolpropane, trimethylolethane, and pentaerythritol.

Examples of tricarboxylic or polycarboxylic acids which can be used in reaction solutions according to variant (b) include 1,2,4-benzenetricarboxylic acid, 1,3,5-benzenetricarboxylic acid, 1,2,4,5-benzenetetracarboxylic acid, and mellitic acid.

The tricarboxylic or polycarboxylic acids may be used either per se or else in the form of derivatives.

By derivatives are meant preferably the corresponding anhydrides in monomeric or polymeric form, mixed anhydrides with other carboxylic acids, such as with acetic acid, monoalkyl, dialkyl or trialkyl esters, preferably monomethyl, dimethyl or trimethyl esters or the corresponding monoethyl, diethyl or triethyl esters, but also those monoesters, diesters and triesters derived from higher alcohols such as n-propanol, isopropanol, n-butanol, isobutanol, tert-butanol, n-pentanol, and n-hexanol, for example, and monovinyl, divinyl or trivinyl esters, and mixed methyl ethyl esters.

In the context of the present invention it is also possible to use a mixture of a tricarboxylic or polycarboxylic acid and one or more of its derivatives. It is likewise possible in the context of the present invention to use a mixture of two or more different derivatives of one or more tricarboxylic or polycarboxylic acids.

Diols for reaction solutions according to variant (b) of the present invention include for example ethylene glycol, propane-1,2-diol, propane-1,3-diol, butane-1,2-diol, butane-1,3-diol, butane-1,4-diol, butane-2,3-diol, pentane-1,2-diol, pentane-1,3-diol, pentane-1,4-diol, pentane-1,5-diol, pentane-2,3-diol, pentane-2,4-diol, hexane-1,2-diol, hexane-1,3-diol, hexane-1,4-diol, hexane-1,5-diol, hexane-1,6-diol, hexane-2,5-diol, heptane-1,2-diol 1,7-heptanediol, 1,8-octanediol, 1,2-octanediol, 1,9-nonanediol, 1,10-decanediol, 1,2-decanediol, 1,12-dodecanediol, 1,2-dodecanediol, 1,5-hexadiene-3,4-diol, cyclopentanediols, cyclohexanediols, inositol and derivatives, 2-methyl-2,4-pentanediol, 2,4-dimethyl-2,4-pentanediol, 2-ethyl-1,3-hexanediol, 2,5-dimethyl-2,5-hexanediol, 2,2,4-trimethyl-1,3-pentanediol, pinacol, diethylene glycol, triethylene glycol, dipropylene glycol, tripropylene glycol, polyethylene glycols HO(CH$_2$CH$_2$O)$_n$—H or polypropylene glycols HO(CH[CH$_3$]CH$_2$O)$_n$—H or mixtures of two or more representatives of the above compounds, with n being an integer and n=4. One or both hydroxyl groups in the abovementioned diols may also be substituted by SH groups. Preference is given to ethylene glycol, propane-1,2-diol, and diethylene glycol, triethylene glycol, dipropylene glycol, and tripropylene glycol.

Reaction solutions which can be reacted according to variant (c) comprise for example one or more triols and one or more tetracarboxylic acids or one or more derivatives thereof. According to variant (c) it is also possible to react one or more tricarboxylic acids or one or more derivatives thereof with one or more tetrafunctional alcohols. The reaction of a trifunctional alcohol with a tricarboxylic acid or derivatives is accomplished by the process of the invention preferably when the hydroxyl groups or the carboxyl groups differ greatly from one another in reactivity.

The molar ratio of hydroxyl to carboxyl groups in variants (a) to (c) are from 3:1 to 0.3:1, preferably from 2:1 to 0.5:1, in particular from 1.5:1 to 0.66:1.

Reaction solutions which can be reacted according to variant (d) comprise one or more di- or polyhydroxycarboxylic acids containing at least 2 hydroxyl groups per molecule, examples being dimethylolpropionic acid, dimethylolbutyric acid, tartaric acid, 3,4-dihydroxyhydrocinnamic acid, 2,3-dihydroxybenzoic acid, 2,4-dihydroxybenzoic acid, 2,5-dihydroxybenzoic acid, 3,4-dihydroxybenzoic acid, and 2,6-dihydroxybenzoic acid, or mixtures thereof.

Reaction solutions which can be reacted according to variant (e) comprise one or more hydroxydi- or hydroxypolycarboxylic acids, examples being tartaric acid, citric acid, maleic acid, 4-hydroxyphthalic acid, 2-hydroxyterephthalic acid or mixtures thereof.

The di- or polyhydroxycarboxylic acids and, respectively, hydroxydi- or hydroxypolycarboxylic acids from variants (d) and (e) may be used either per se or else in the form of derivatives.

By derivatives of di- or polyhydroxycarboxylic acids and, respectively, hydroxydi- or hydroxypolycarboxylic acids used in reaction solutions according to variants (d) and (e) are meant preferably
  the corresponding anhydrides in monomeric, dimeric or polymeric form,
  cyclic dimerization products,
  esters with other carboxylic acids, such as with acetic acid,
  monoalkyl or dialkyl esters, preferably monomethyl or dimethyl esters or the corresponding monoethyl or diethyl esters, but also the esters derived from higher alcohols such as n-propanol, isopropanol, n-butanol, isobutanol, tert-butanol, n-pentanol, and n-hexanol, for example,
  monovinyl and divinyl esters, and
  mixed esters, preferably methyl ethyl esters.

In the context of the present invention it is likewise possible to use di- or polyhydroxycarboxylic acids and, respectively, hydroxydi- or hydroxypolycarboxylic acids and one or more of their derivatives. It is likewise possible in the context of the present invention to use a mixture of two or more different derivatives of one or more di- or polyhydroxycarboxylic acids and, respectively, hydroxydi- or hydroxypolycarboxylic acids.

In the context of the present invention it is likewise possible to react mixtures of at least two of the above reaction solutions of variants (a) to (e): for example, a mixture of a reaction solution according to variant (a) with a reaction solution according to variant (d) or (e).

By reaction solution is meant, in the context of the present invention, in variants (a) to (c), the mixtures of
  compounds carrying hydroxyl and carboxyl groups,
  solvent,
  and any additives.

In the case of variants (d) and (e) reaction solutions in the context of the present invention are the mixtures of
  one or more di- or polyhydroxycarboxylic acids and, respectively, hydroxydi- or hydroxypolycarboxylic acids or corresponding derivatives
  with solvent and any additives.

A preferred procedure is to remove the water formed during the reaction, preferably by operating in the presence of a water remover additive added at the beginning of the reaction. Suitable examples include weakly acidic silica gels, weakly acidic aluminum oxides, molecular sieves, especially 4 Å molecular sieve, MgSO$_4$, and Na$_2$SO$_4$. The use of strongly acidic silica gels is likewise possible. Additionally, further water remover can be added during the reaction, or water remover can be replaced by fresh water remover.

The process of the invention is conducted in the presence of an enzyme. Preference is given to using lipases or esterases. Highly suitable lipases and esterases are, for example, from *Burkholderia Alantarii, Candida cylindracea, Candida lipolytica, Candida rugosa, Candida antarctica, Candida utilis, Chromobacterium viscosum, Geotrichum viscosum, Geotrichum candidum, Mucor javanicus, Mucor mihei*, pig pancreas, *Pseudomonas* spp., *Pseudomonas fluorescens, Pseudomonas cepacia, Rhizopus arrhizus, Rhizopus delemar, Rhizopus niveus, Rhizopus oryzae, Aspergillus niger, Penicillium roquefortii, Penicillium camembertii* or esterase from *Bacillus* spp. and *Bacillus thermoglucosidasius*. Particular preference is given to *Candida antarctica* Lipase B. The enzymes listed are available commercially, from Novozymes Biotech Inc., Denmark, for example.

The enzyme is preferably used in immobilized form, on silica gel or Lewatit®, for example. Methods of immobilizing enzymes are known per se from, for example, Kurt Faber, "Biotransformations in organic chemistry", 3rd Edition 1997, Springer Verlag, section 3.2 "Immobilization" pages 345-356. Immobilized enzymes are available commercially, from Novozymes Biotech Inc., Denmark, for example.

The amount of immobilized enzyme used is from 0.1 to 20% by weight, in particular 10-15% by weight, based on the mass of all of the reaction starting materials used.

The process of the invention is conducted at temperatures above 60° C. It is preferred to operate at temperatures of 100° C. or below. Preference is given to temperatures up to 80° C., with very particular preference from 62 to 75° C., and more preferably still from 65 to 75° C.

The process of the invention is conducted in the presence of a solvent. Suitable examples include hydrocarbons such as paraffins or aromatics. Particularly suitable paraffins are n-heptane and cyclohexane. Particularly suitable aromatics are toluene, ortho-xylene, meta-xylene, para-xylene, xylene isomer mixture, ethylbenzene, chlorobenzene, and ortho- and meta-dichlorobenzene. Further especially suitable solvents include ethers such as dioxane or tetrahydrofuran, for example, and ketones such as methyl ethyl ketone and methyl isobutyl ketone, for example.

The amount of solvent added is at least 5 parts by weight, based on the mass of the reaction starting materials used, preferably at least 50 parts by weight, and with particular preference at least 100 parts by weight. Amounts of more than 10,000 parts by weight of solvent are undesirable since at markedly lower concentrations the rate of reaction subsides considerably, leading to uneconomically long reaction times.

The process of the invention is conducted at pressures above 500 mbar. It is preferred to react at atmospheric pressure or slightly elevated pressure, up to 1200 mbar for example. It is also possible to operate under considerably increased pressure, examples being pressures up to 10 bar. Reaction at atmospheric pressure is preferred.

The reaction time of the process of the invention is normally from 4 hours to 6 days, preferably from 5 hours to 5 days, and with particular preference from 8 hours to 4 days.

After the end of the reaction the highly functional hyperbranched polyesters can be isolated, for example, by filtering off the enzyme and concentrating the filtrate, normally under reduced pressure. Further highly suitable workup methods are precipitation following addition of water, and subsequently washing and drying of the precipitate.

The present invention further provides the highly functional hyperbranched polyesters obtainable by the process of the invention. They are distinguished by low levels of discoloration and resinification. On the definition of hyperbranched polymers see also P. J. Flory, J. Am. Chem. Soc. 1952, 74, 2718 and A. Sunder et al., Chem. Eur. J. 2000, 6, No. 1, 1-8. In the context of the present invention, however, "highly functional hyperbranched" means that there is one branch with one functional group in at least 20 mol % of each second monomer unit in the case of variants (a) to (c) and one branch with a functional group in every monomer unit in the case of variants (d) and (e).

The polyesters of the invention have a molecular weight $M_n$ of from 1000 to 30,000 g/mol, preferably from 2000 to 20,000 g/mol, with particular preference from 3000 to 7000 g/mol, and with very particular preference 4000 g/mol. The polydispersity is from 1.2 to 50, preferably from 1.4 to 40, with particular preference from 1.5 to 30, and with very particular preference up to 10.

The highly functional hyperbranched polyesters of the invention are carboxy-terminated, carboxy- and hydroxyl-terminated, and, preferably, hydroxyl-terminated and can be used with advantage for preparing, for example, adhesives, coatings, foams, coverings, and paints.

The present invention additionally provides for the use of the highly functional hyperbranched polyesters of the invention for preparing polyadducts or polycondensates, examples being polycarbonates, polyurethanes, polyethers, and linear polyesters. It is preferred to use the hydroxyl-terminated highly functional hyperbranched polyesters of the invention for preparing polyadducts or polycondensates, such as polycarbonates or polyurethanes, for example.

The present invention further provides for the use of the highly functional hyperbranched polyesters of the invention and of the polyadducts or polycondensates prepared from highly functional hyperbranched polyesters as a component of adhesives, coatings, foams, coverings, and paints. The present invention additionally provides adhesives, coatings, foams, coverings, and paints comprising the highly functional hyperbranched polyesters of the invention or polyadducts or polycondensates prepared from the highly functional hyperbranched polyesters of the invention. They are distinguished by outstanding performance properties.

The invention is illustrated by examples.

EXAMPLE 1

In a 1 L round-bottomed flask 105.2 g (0.72 mol) of adipic acid and 55.2 g (0.60 mol) of glycerol were dissolved in absolute dioxane (300 g). Molecular sieve (30 g, 0.4 nm) was then added, followed by immobilized lipase from *Candida antarctica* B (Novozym® 435, 20 g). The reaction mixture was stirred under atmospheric pressure at 70° C. for 95 h. It was then cooled to room temperature and the enzyme was filtered off. Removal of the solvent under reduced pressure gave 138 g of a colorless viscous oil which dissolved readily in THF.

$M_n$=3180 g
$M_w$=30052 g
Acid number: 42 mg KOH/g
Polydispersity: 9.5, determined by gel permeation chromatography with polystyrene calibration

EXAMPLE 2

In a 100 mL round-bottomed flask 6.78 g of azelaic acid (36 mmol) and 2.76 g of glycerol (30 mmol) were reacted with one another in 40 g of absolute dioxane in the presence of Novozym® 435 (1.5 g) and molecular sieve (4 g, 0.4 nm). After 5 days of stirring at 70° C. the reaction mixture was cooled to room temperature, the enzyme was filtered off and the solvent was distilled off under reduced pressure. This gave 7.9 g of a colorless oil which dissolved readily in THF.

$M_n$=4743 g
$M_w$=8614 g
Acid number: 161 mg/KOH/g
Polydispersity: 1.8

EXAMPLE 3

In a 100 mL round-bottomed flask 25.1 g of dimethyl adipate (144 mmol) and 11.1 g of glycerol (120 mmol) were reacted in absolute THF (20 mL) with addition of Novozym® 435 (5 g) and molecular sieve (30 g, 0.4 nm) at 70° C. under atmospheric pressure. After 5 days the reaction mixture was cooled to room temperature, the enzyme was filtered off and the solvent was distilled off under reduced pressure. This gave 20.5 g of a colorless oil which dissolved readily in THF.

$M_n$=8630 g
$M_w$=91.743 g
Acid number: 6.2 mg/KOH/g
Polydispersity: 1.1

We claim:

1. A highly functional hyperbranched polyester obtained by a process which comprises reacting a reaction solution comprising solvent and
   (a) one or more dicarboxylic acids or one or more derivatives thereof with one or more at least trifunctional alcohols,
   (b) one or more tricarboxylic acids or higher polycarboxylic acids or one or more derivatives thereof with one or more diols,
   (c) one or more tricarboxylic acids or higher polycarboxylic acids or one or more derivatives thereof with one or more at least trifunctional alcohols,
   (d) one or more di- or polyhydroxycarboxylic acids, (e) one or more hydroxydi- or hydroxypolycarboxylic acids, or (f) a mixture of at least two of (a), (b), (c), (d) and (e), in the presence of an enzyme at a temperature above 60° C. and a pressure above 500 mbar.

2. The polyester of claim 1, wherein water formed during the reaction is removed.

3. The polyester of claim 1, wherein the enzyme is a lipase.

4. The polyester of claim 1, wherein the lipase is *Candida antarctica* lipase B.

5. The polyester of claim 1, wherein the enzyme is used in immobilized form.

6. The polyester of claim 1, wherein the process is carried out at temperatures above 60° C. up to 80° C.

7. The polyester of claim 1, wherein said derivatives of the di-, tri- or polycarboxylic acids are the respective methyl or ethyl esters.

8. The polyester of claim 1, which is molecularly and structurally nonuniform.

9. The polyester of claim 1, which is obtained by a process which comprises reacting a reaction solution comprising solvent and (a) one or more dicarboxylic acids or one or more derivatives thereof with one or more at least trifunctional alcohols.

10. The polyester of claim 1, which is obtained by a process which comprises reacting a reaction solution comprising solvent and (b) one or more tricarboxylic acids or higher polycarboxylic acids or one or more derivatives thereof with one or more diols.

11. The polyester of claim 1, which is obtained by a process which comprises reacting a reaction solution comprising solvent and (c) one or more tricarboxylic acids or higher polycarboxylic acids or one or more derivatives thereof with one or more at least trifunctional alcohols.

12. The polyester of claim 1, which is obtained by a process which comprises reacting a reaction solution comprising solvent and (d) one or more di- or polyhydroxycarboxylic acids.

13. The polyester of claim 1, which is obtained by a process which comprises reacting a reaction solution comprising solvent and (e) one or more hydroxydi- or hydroxypolycarboxylic acids.

14. The polyester of claim 1, which is obtained by a process which comprises reacting a reaction solution comprising solvent and (f) a mixture of at least two of (a), (b), (c), (d) and (e).

15. The polyester of claim 1, wherein the enzyme is an esterase.

16. The polyester of claim 1, wherein the enzyme is immobilized on silica gel.

17. The polyester of claim 1, wherein the amount of enzyme is from 0.1 to 20% by weight based on the mass of the starting materials (a), (b), (c), (d), (e) or (f).

18. A process for preparing a polyadduct or polycondensate comprising preparing a polyadduct or a polycondensate from the polyester of claim 1.

19. The polyadduct or polycondensate obtained by the process of claim 18.

20. A process for preparing adhesives, coatings, foams, paints, and coverings, comprising incorporating the polyadduct or polycondensate of claim 18 into an adhesive, coating, foam, paint, or covering.

21. An adhesive, coating, foam, paint, or covering obtained by the process of claim 20.

22. A process for preparing the polyester of claim 1, comprising reacting a reaction solution comprising solvent and (a) one or more dicarboxylic acids or one or more derivatives thereof with one or more at least trifunctional alcohols, (b) one or more tricarboxylic acids or higher polycarboxylic acids or one or more derivatives thereof with one or more diols, (c) one or more tricarboxylic acids or higher polycarboxylic acids or one or more derivatives thereof with one or more at least trifunctional alcohols, (d) one or more di- or polyhydroxycarboxylic acids, (e) one or more hydroxydi- or hydroxypolycarboxylic acids, or (f) a mixture of at least two of (a), (b), (c), (d) and (e), in the presence of an enzyme at a temperature above 60° C. and a pressure above 500 mbar.

23. A highly functional hyperbranched polyester obtained by the polymerization of (a) one or more dicarboxylic acids or one or more derivatives thereof with one or more at least trifunctional alcohols, (b) one or more tricarboxylic acids or higher polycarboxylic acids or one or more derivatives thereof with one or more diols, (c) one or more tricarboxylic acids or higher polycarboxylic acids or one or more derivatives thereof with one or more at least trifunctional alcohols, (d) one or more di- or polyhydroxycarboxylic acids, (e) one or more hydroxydi- or hydroxypolycarboxylic acids, or (f) a mixture of at least two of (a), (b), (c), (d) and (e).

\* \* \* \* \*